United States Patent [19]
Higuchi et al.

[11] 4,057,619
[45] *Nov. 8, 1977

[54] OCULAR THERAPEUTIC SYSTEM WITH SELECTED MEMBRANES FOR ADMINISTERING OPHTHALMIC DRUG

[75] Inventors: Takeru Higuchi, Lawrence, Kans.; Anwar Hussain, Lexington, Ky.

[73] Assignee: Alza Corporation, Palo Alto, Calif.

[*] Notice: The portion of the term of this patent subsequent to Sept. 9, 1992, has been disclaimed.

[21] Appl. No.: 705,470

[22] Filed: July 15, 1976

Related U.S. Application Data

[63] Continuation-in-part of Ser. No. 591,712, June 30, 1975, abandoned, which is a continuation-in-part of Ser. No. 281,446, Aug. 17, 1972, Pat. No. 3,903,880, which is a continuation-in-part of Ser. No. 80,531, Oct. 14, 1970, abandoned.

[51] Int. Cl.² ............ A61K 9/00; A61K 9/22
[52] U.S. Cl. .................... 424/14; 128/260; 424/16; 424/19; 424/22; 424/28
[58] Field of Search .......... 128/260; 424/14–22, 424/28

[56] References Cited

U.S. PATENT DOCUMENTS

| | | | |
|---|---|---|---|
| 2,200,429 | 5/1940 | Perrin et al. | 526/235 |
| 2,396,785 | 3/1946 | Hanford | 526/232 |
| 2,947,735 | 8/1960 | Bartl | 526/212 |
| 3,710,795 | 1/1973 | Higuchi et al. | 128/260 |
| 3,854,480 | 12/1974 | Zaffaroni | 128/260 |

FOREIGN PATENT DOCUMENTS

569,927  6/1945  United Kingdom.
582,093  11/1946  United Kingdom.

OTHER PUBLICATIONS

Raff et al., Crystalline Olefin Polymers, Raff et al., part II, pp. 261–266 (1964).

*Primary Examiner* — Shep K. Rose
*Attorney, Agent, or Firm* — Paul L. Sabatine; Thomas E. Ciotti; Edward L. Mandell

[57] ABSTRACT

An ocular therapeutic system for releasing a drug to the eye at a controlled and continuous rate for a prolonged period of time is disclosed. The system is shaped, sized and adapted for insertion and retention in the eye. The system contains an ophthalmically acceptable drug and it is formed of a polymeric material permeable to the passage of drug by diffusion. The material is an ethylene-vinyl ester copolymer of the general formula:

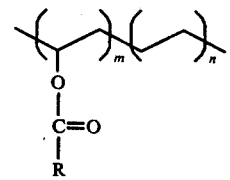

wherein R is hydrogen, alkyl of 2 to 7 carbons, or aryl, $m$ is (4 to 80)% by weight and $n$ is $(100 - m)$% by weight.

13 Claims, 4 Drawing Figures

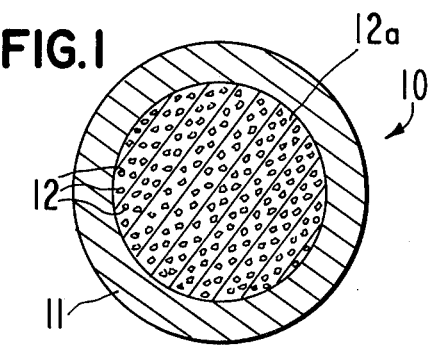
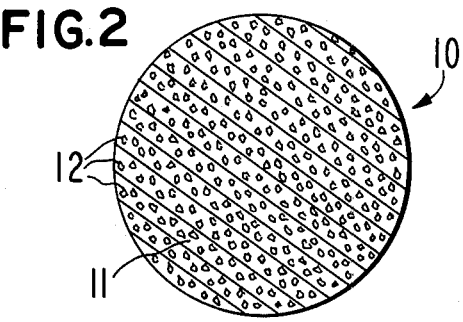
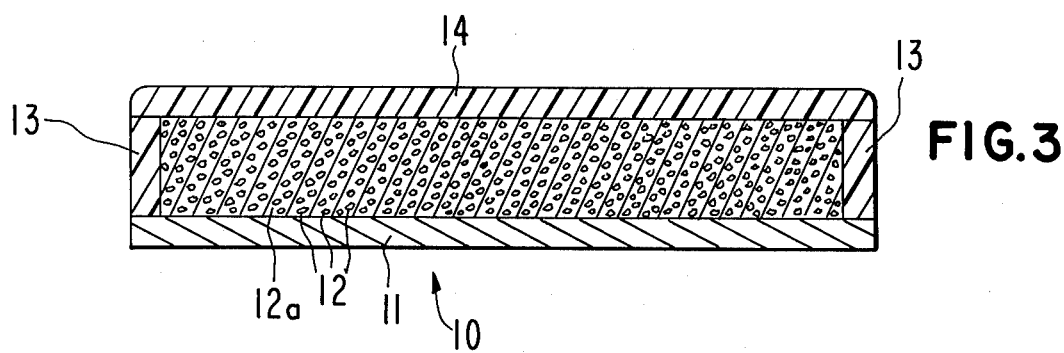
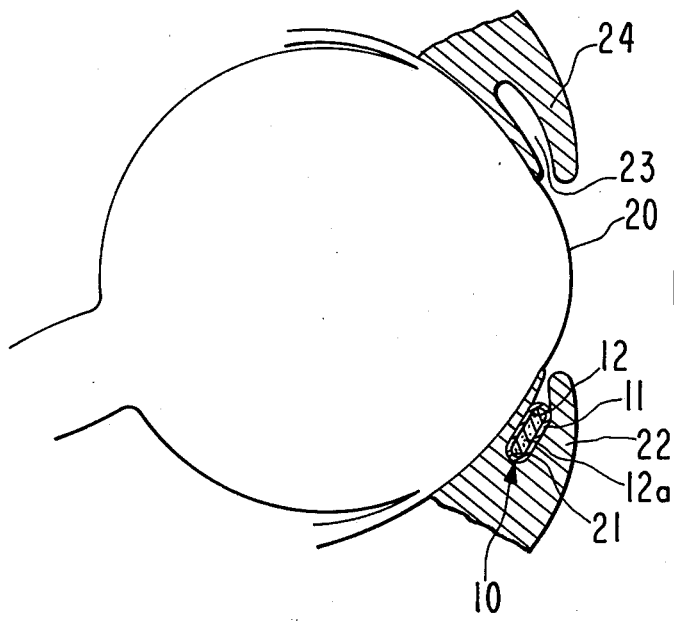

OCULAR THERAPEUTIC SYSTEM WITH SELECTED MEMBRANES FOR ADMINISTERING OPHTHALMIC DRUG

CROSS-REFERENCE TO RELATED APPLICATIONS

This application is a continuation-in-part of U.S. patent application Ser. No. 591,712 filed on June 30, 1975 now abandoned, which application is a continuation-in-part of U.S. patent application Ser. No. 281,446 filed on Aug. 17, 1972, and now U.S. Pat. No. 3,903,880, which application is a continuation-in-part of U.S. patent application Ser. No. 80,531 filed on Oct. 14, 1970, now abandoned. These applications are assigned to the same assignee of this application, and benefit of all their filing dates is claimed.

FIELD OF THE INVENTION

This invention relates to a novel and useful ocular delivery system for releasing a pharmaceutically acceptable drug at a controlled and continuous rate for a prolonged period of time to the eye to produce a physiological or pharmacological effect. The ocular delivery system is comprised of a drug release rate controlling polymeric material surrounding at least a part of the drug, or the material contains the drug therein. The material is permeable to the passage of drug by diffusion.

BACKGROUND OF THE INVENTION

Often, the ophthalmic medical and veterinary programs, it is desirable and important to provide for the slow release of a drug to the eye at a controlled and continuous rate over a prolonged period of time. In many programs such a rate of release should be substantially constant or have a zero order time dependence, that is, the rate of release is independent of time.

Different approaches have heretobefore been tried in ophthalmology to obtain a device for releasing drug to the eye at a controlled and continuous rate. One approach, which has received great attention, is to mix the drug with a carrier that is gradually broken down by eye fluids, the drug being released as the carrier disintegrates. Numerous carriers have been used in such systems, including soluble polymers such as gelatin and collagen. While these systems have provided a slower release of drug, a controlled and continuous release at a substantially constant release rate has not been obtained. One reason for this is that as the carrier disintegrates, the surface area of the dosage unit decreases, concomitantly exposing increasingly smaller quantities of the carrier to the surrounding eye fluids. This inherently results in a decline in the release rate over time. There has been little success in gaining control over drug release rate by this approach. More recently, in U.S. Pat. No. 3,618,604 there is disclosed an ocular drug delivery device that represents a substantial improvement over previously proposed drug devices and which devices can be successfully used for their intended purpose in the management of ocular medicine. But, the use of some of the polymeric materials set forth therein, for example, partially hydrolyzed polvinyl acetate because of its gel-like properties, has led to manufacturing difficulties and has not given the desired drug release rates in many instances.

In unrelated, non-ophthalmic fields, polymeric materials have been used for releasing non-ophthalmic substances. For example, in U.S. Pat. No. 3,310,235 a device is disclosed made of the material ethylene-vinyl acetate copolymer, as seemingly suitable for releasing volatile, organic and toxic phosphorous biocides by the process of physical evaporation. With this device, biocide release is achieved by evaporation from the surface, and if the ingredient is not sufficiently volatile at the temperature of use, the device has no practical value. Evaporation is achieved by using a woven cloth which acts as an evaporation surface. Release rate by evaporation is difficult to regulate and virtually impossible to control, as it is subjected to uncontrollable environmental conditions, the vapor pressure of the substance, and the degree of saturation of the volatile substance in the environment. This type of clearance inherently defeats the basic purpose of providing a device for ophthalmic use which requires release of drug at a controlled and continuous rate for a prolonged period of time as by the process of diffusion. Other incidental and non-therapeutic uses for ethylene-vinyl acetate copolymer are disclosed in U.S. Pat. No. 3,400,011 wherein the polymeric material is mixed with waxes and used for coating ingredients that are substantially released by the movement of external fluids into the coating, causing it to rupture and release the ingredient; in French Patent No. 1,489,490 as a thickener; and in French Patent No. 1,505,267 as a non-diffusional formless base for chewing gum. In our copending continuation U.S. patent application Ser. No. 705,479 filed concurrently herewith on July 15, 1976 and further identified by attorney Docket No. I.R. 176C-CONT., drug delivery devices including ocular devices manufactured from ethylene-vinyl acetate copolymers are disclosed for releasing drugs at controlled rates to animals. The devices claimed in said copending application are ocular devices and they are used for releasing drug to the eye. In this application, it has now been found that other ethylene-vinyl ester copolymers can be inventively used for manufacturing ocular systems designed in the form of ocular devices for releasing drug to the eye at a controlled rate over a prolonged period of time.

OBJECTS OF THE INVENTION

One important object of this invention is to provide a novel and useful shaped drug delivery system manufactured in the form of an ocular device for use in the eye for prolongedly releasing drug at a controlled rate, by providing a material that has the ability to give therapeutically operable drug release rates in the eye while simultaneously remaining substantially free of any adverse unwanted toxic effects to the host.

Still another object of this invention is to provide a medical and veterinary useful ocular delivery system which can release drug at a rate which does not vary with time.

Yet a further object of this invention is to provide an ocular drug delivery system fabricated from a material which is compatible with body tissue and exhibits substantially no toxicity thereto.

Still yet another object of the invention is to provide a reliable and easily used ocular drug delivery system for continuously administered controlled quantities of drug to the eye or to an eye and its surrounding receptor sites.

Still a further and immediate object of this invention is to provide an ocular drug delivery system for the administration of a locally acting or systemically acting eye drug to produce a physiological or pharmacological effect.

Still another object of the invention is to provide a drug delivery system made from a material that can be handled, for example, heat sealed, without substantially adversely effecting the properties of the drug, particularly an ocular drug as contained therein.

Yet a further object of the invention is to provide an ocular system designed as an ocular device and formed of a drug release rate controlling material permeable to the passage of drug by diffusion which process is the drug release rate controlling means for releasing drug from the system.

Other objects of this invention will become more apparent to those skilled in the art from the following detailed description of the invention, taken in conjunction with the drawings, and the accompanying claims.

SUMMARY OF THE INVENTION

In accomplishing the objects, features and advantages of this invention, it has now been found that an ocular system for releasing drug over a prolonged period of time comprising a drug reservoir and a polymeric barrier through which the drug passes by diffusion, can be provided by using an ethylene-vinyl ester copolymer as the polymeric material. In a presently preferred embodiment, the invention resides in an eye medication dispensing device which is a flexible body of an ethylene-vinyl ester copolymer having a vinyl ester content of about 4 to 80% by weight. The system contains an ophthalmic drug which is dispensed to the eye by diffusion through the copolymer. The system is adapted for insertion in the cul-de-sac of the conjunctiva between the sclera of the eyeball and the lid, to be held in place against the eyeball by the pressure of the lid.

BRIEF DESCRIPTION OF THE DRAWINGS

In the drawings, which are not drawn to scale, but are set forth to illustrate various embodiments of the invention, and wherein like reference numerals designate like parts, the figures are as follows:

FIG. 1 is a side cross-sectional view of an ocular drug delivery system of the invention comprised of a wall surrounding a reservoir containing drug;

FIG. 2 is a side cross-sectional view of another embodiment of the drug delivery system of the invention comprised of a system having drug therein;

FIG. 3 is a side cross-sectional view of another embodiment of the invention in the form of a rectangular system; and, FIG. 4 is a side view, partially in cross-section of the system of the invention with the medication dispensing system seen in an eye.

DETAILED DESCRIPTION OF THE DRAWINGS

In accordance with this invention, it has now been unexpectedly found that ethylene-vinyl ester copolymers can be successfully manufactured into novel and useful ocular drug delivery system and can therefore be used for the controlled release of drugs to the eye by diffusion.

As illustrated in FIG. 1, the novel and useful ocular drug delivery system 10 of the invention can have a wall 11 fabricated of ethylene-vinyl ester copolymer enclosing a reservoir 12a containing a drug 12. Drug 12 is one capable of diffusing through ethylene-vinyl ester copolymer walls 11. Alternatively, as illustrated in FIG. 2, ocular drug delivery system 10 can be comprised of a solid matrix 11 of ethylene-vinyl ester copolymer, which also serves as a drug reservoir, having drug 12 distributed therefore.

Essential to this invention is the use of an ethylene-vinyl ester copolymer as the rate limiting barrier for the controlled and continuous release of drugs by diffusion. This requires that the ocular system have at least one barrier or wall of biologically acceptable ethylene-vinyl ester copolymer through which the drug will pass by diffusion. Various forms of the invention are included within this framework. Thus, the system of the invention can have a single ethylene-vinyl ester membrane on one surface thereof and through which the drug will pass by diffusion. One form of this embodiment is illustrated in FIG. 3, a detailed description of which is presented later in the specification. In another embodiment of the invention, the system is a biologically acceptable container, with walls of ethylene-vinyl ester copolymer, and the drug in the interior thereof; see FIG. 1 for example. In this form of the invention, drug alone can be within the interior reservoir of the system or the drug can be dispersed in a liquid, semi-solid, or solid matrix and the matrix enclosed within the ethylene-vinyl ester copolymer barrier. In each of these embodiments, passage of the drug by diffusion through the ethylene-vinyl ester copolymer is the rate controlling step for drug administration. For further details of such a drug delivery system in which the drug is dispersed throughout a solid matrix enclosed within a barrier through which drug can pass by diffusion, reference is made to U.S. Pat. No. 3,854,480 for an invention of Alejandro Zaffaroni assigned to the assignee of this invention. The disclosure of that application is relied upon and incorporated herein by reference. In another embodiment of the invention (as in FIG. 2), the drug 12 is distributed throughout a matrix, which matrix in this embodiment is a reservoir 12a, of ethylene-vinyl ester copolymer 11. Preferably, solid particles or a liquid form of the drug are used, although the drug can be in solution in the polymeric matrix.

Drug delivery systems of the invention can take a wide variety of shapes and forms for administering the drugs to the eye at controlled and continuous rates. In each instance, the drug delivery system has an ethylene-vinyl ester copolymer barrier for release of the drug by diffusion. For example, as illustrated in FIG. 3, rectangular shaped system 10 is comprised of a film 11 of ethylene-vinyl ester copolymer on one surface of a reservoir 12a containing drug 12. The reservoir is bounded by side walls 13 and top surface wall 14. This system is shaped, sized and adapted to release drug beneath the eyelid by diffusion through film 11 at a predetermined rate.

FIG. 4 illustrates eye medication dispensing system 10 delivering drug to an eye. System 10 is made of a flexible bodies of ethylene-vinyl ester copolymer containing an ophthalmic drug, such as pilocarpine, which is dispensed to the eye by diffusion through the copolymer. The system is shaped and size adapted for insertion in the cul-de-sac of the conjunctiva between the sclera of the eyeball and the lid, to be held in place against the eyeball by the pressure of the lid. As illustrated in FIG. 4, system 10 of the invention can have ethylene-vinyl ester walls 11 surrounding a reservoir 12a containing ophthalmic drug 12. In use, drug 12 is dispensed to eyeball 20 by diffusion through ethylene-vinyl ester walls 11. System 10 is illustrated at being placed in lower cul-de-sac 21 of the conjunctiva between the sclera of the eyeball and the lower lid 22. Alternatively, system 10 can be placed in upper cul-de-sac 23 of the conjunctiva between the sclera of the eyeball and the upper eyelid 24. In either case, it is held in place against the eyeball by the pressure of the lid. For further details on these eye medication dispensing systems, reference is made to U.S. Pat. No. 3,416,530 and to co-pending patent application Ser. No. 831,761 filed June 9, 1969, now U.S. Pat. No. 3,618,604. Both of these patents are assigned to the assignee of this invention. The disclosure of that co-pending application is relied upon and incorporated herein by reference. One important advantage in using ethylene-vinyl ester copolymers in such eye medication dispensing systems, is that precise control over the rate of release of ophthalmic drugs, especially pilocarpine, is obtained with the drug being released at a therapeutically effective rate.

DETAILED DESCRIPTION OF THE INVENTION

In accordance with the practice of this invention, it has now been found the polymeric material ethylene-vinyl ester copolymers of the general formula:

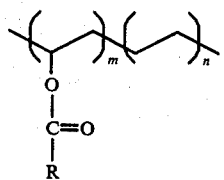

wherein R is hydrogen, lower alkyl of 2 to 7 carbons and aryl, and $m$ is (4 to 80)% by weight and $n$ is (100 − $m$)% by weight, can be successfully used to provide ocular delivery devices. Typical alkyl groups include ethyl, propyl, isopropyl, butyl, tert-butyl, pentyl and hexyl. Typical aryl groups include phenyl.

The ethylene-vinyl ester copolymers are made by the copolymerization of ethylene with vinyl esters of the formula $$CH_2=CH-O-\overset{O}{\underset{\|}{C}}-R$$

wherein R is as defined. Typical esters, named as the substituted acetate, include vinyl formate $$CH_2=CH-O-\overset{O}{\underset{\|}{C}}-H,$$

vinyl butyl acetate

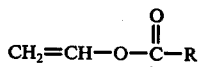

also known as vinyl hexanoate vinyl methyl acetate

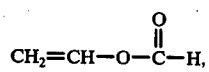

also known as vinyl propionate vinyl ethyl acetate

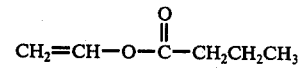

also known as vinyl butyrate vinyl propylacetate

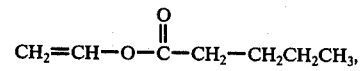

also known as vinyl pentanoate vinyl trimethylacetate

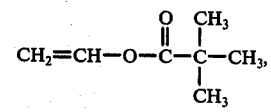

vinyl diethylacetate

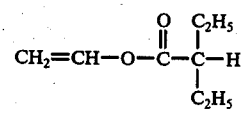

also known as 2 ethylbutanoate vinyl isopropylacetate

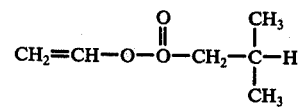

also known as 3-methylbutanoate vinyl tert-butylacetate

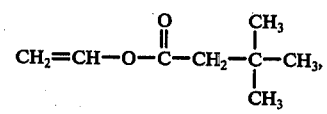

also known as 3,3-dimethylbutanoate vinyl phenylacetate

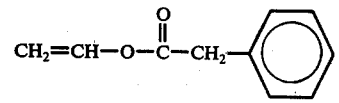

and vinyl benzoate

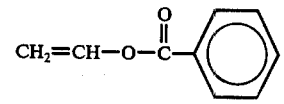

Representative ethylene-vinyl ester copolymers suitable for providing ocular devices, with the copolymers named as acetates, include ethylene-vinyl formate, ethylene-vinyl butyl acetate, ethylene-vinyl methylacetate, also known as ethylene-vinyl propionate. ethylene-vinyl ethylacetate, also known as ethylene-vinyl butyrate, ethylene-vinyl propylacetate, also known as ethylene-vinyl pentanoate and the like.

Ethylene-vinyl ester copolymers are well known commercially available materials. Exemplary techniques for their preparation are described in U.S. Pat. Nos. 2,200,429, 2,396,785, and 2,947,735, in British Patent Nos. 569,927 and 582,093, and in Crystalline Olefin Polymers, Editors Raff, R.A.V. and Doak, K.W., Part II, pages 261 to 266, 1964, published by Interscience Publishers, New York. In its broadest aspects, the present invention contemplates use of ethylene-vinyl ester copolymers and preferably, ethylene-vinyl ester copolymers, having a vinyl ester

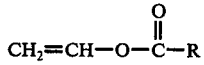

content of about 4 to 80% by weight of the total, a melt index of about 0.1 to 1000 grams per ten minutes, a density of 0.920 to 1.25, and a frequency of acyloxy groups (RCO) on the polyethylene backbone of 1/200 to 1/3.5. In a preferred embodiment, the ethylene-vinyl ester copolymer has a vinyl ester content of about 4 to 50% by weight, a melt index of about 0.5 to 500 grams per ten minutes, a density having a range of about 0.920 to 1.190, and a frequency of acyloxy groups on the polyethylene backbone of 1/150 to 1/8. More preferably, the copolymer has a vinyl ester content of 4 to 40% by weight and a melt index of about 0.5 to 25 grams per ten minutes. Moreover, it has been surprisingly found that the absolute release rate of drug through this ethylene-vinyl ester copolymer barrier can be varied and accurately controlled by selecting a copolymer having the frequency of acyloxy groups with an alkyl moiety of 2 to 7 carbons within the range set forth above. Melt index is the number of grams of copolymer which can be forced through a standard cylindrical orifice under a standard pressure at a standard temperature and thus is inversely related to a molecular weight. As used in this specification and the appended claims, melt index is as determined in accordance with standard ASTM D 1238'-65T condition E practice.

The ethylene-vinyl ester copolymer and preferably the ethylene-vinyl lower alkyl substituted acetate copolymer, act as the rate controlling barrier as they are permeable to drugs, and they permit passage of the drug by diffusion through the copolymer at a relatively low to relatively high rate. Normally, the rate of passage of the drug through the copolymer is dependent on the solubility of the drug therein, as well as on the thickness of the polymeric barrier. This means that selection of particular copolymers, such as ethylene-vinyl ester compositions, will be dependent on the particular drug to be used. By varying the composition and thickness of the rate controlling barrier, the dosage rate per area of the system can be controlled; as the copolymer acts to meter the flow or diffusion of drug to the exterior of the device. Thus, systems of the same surface area can provide different dosage of a drug by varying the characteristics of the copolymer.

In addition to varying the percentage of vinyl ester, such as vinyl methyl acetate in the copolymer and the melt index or molecular weight, the properties of the copolymer can be changed by selectively hydrolyzing for example the acyloxy groups to alcohol groups. That is, by converting in portion of the vinyl ester units of the copolymer to vinyl alcohol units, the copolymer is rendered more hydrophilic and the rate of passage of relatively hydrophilic drug molecules is increased. The percentage of units hydrolyzed to vinyl alcohol units can vary widely but typically, from about 20 to 60% are converted. This partial hydrolysis is a well known procedure and can be accomplished under standard conditions well known in themselves. Exemplary hydrolysis procedures are set forth in U.S. Pat. Nos. 2,386,347, 2,399,653, 3,386,978, 3,494,908, and the like.

Permeability of the copolymer to drugs by diffusion also can be varied by incorporating fillers into the copolymer. Typical fillers that can be employed in practice of the invention are silica, clay, barytes, carbon black, lithopone, zinc oxide, etc. It should be realized that use of many of these fillers will affect the melt index of the copolymer. However, when melt index is used herein to define the copolymer, it is used as a measure of molecular weight and refers to the melt index of the particular copolymer composition without any filler present. Additionally, in those instances where the rate of release of drug is less than a preselected rate, the drug can be converted to known derivatives that have a greater permeability of drug through the membrane to increase the rate of release. Also, where the rate of drug diffusion is too slow, the rate can easily be increased by using drug delivery devices as embodied in FIG. 2.

Selection of the particular copolymer is governed in large part by the drug to be incorporated in the system, as well as by the desired rate of release of the drug. Those skilled in the art can readily determine the rate of diffusion of drugs through these copolymers and select suitable combinations of copolymer and drug for particular applications. Various techniques can be used to determine the permeability of the copolymers to different drugs. One that has been found to be eminently well suited is to cast or hot press a film of the copolymer to a thickness in the range of 2 to 60 mils. The film is used as a barrier between a rapidly stirred (e.g. 150 r.p.m.) saturated solution of the drug and a rapidly stirred solvent bath, both maintained at constant temperature (typically 37° C). Samples are periodically withdrawn from the solvent bath and analyzed for drug concentration. By plotting drug concentration in the solvent bath versus time, the permeability constant P of the film is determined by the Fick's First Law of Diffusion.

Slope of plot = $(Q_1 - Q_2)/(t_1 - t_2) = P(AC/h)$ wherein $Q_1$ = cumulative amount of drug in solvent in micrograms at $t_1$; $Q_2$ = cumulative amount of drug in solvent in micrograms at $t_2$; $t_1$ = elasped time to first sample, i.e., $Q_1$; $t_2$ = elapsed time to second sample, i.e., $Q_2$; A = area of film in cm$^2$; C = initial concentration of drug in saturated solution at $t$; h = thickness of film in cm. By determining the slope of the plot, i.e., $[(Q_1 - Q_2)/(t_1 - t_2)]$, and solving the equation using the known or measured values of A, C, and h, the permeability P constant in cm$^2$/time of the film for a given drug is readily determined. Of course, this permeability constant is an inherent characteristic of a copolymer of particular composition and melt index, and is unchanged whether the material is used as a matrix or as a film wall. The procedures used to determine the rate of drug release through the copolymer can easily be ascertained by standard techniques known to the art as recorded in J. Pharm. Sci., Vol. 52, pages 1145 to 1149, 1963; ibid., Vol. 53, pages 798 to 802, 1964; ibid., Vol. 54, pages 1459 to 1464, 1965; ibid., Vol. 55, pages 840 to 843, and 1224 to 1239, 1966; Encyl. Polymer. Sci. Technol., Vol. 5 and 9, pages 65 to 82, and 794 to 807, 1968; the reference cited therein, and the like.

The rate of solubilization, or the rate at which drug will go into solution or dissolve in a vehicle confined within the reservoir is quantitatively governed by known physico-chemical principles. For an example, a drug particle dispersed in a vehicle is surrounded by a thin layer of vehicle having a finite thickness l in cm. This layer is considered as an integral part of the drug and it is characteristically referred to as the "stagnant layer". The stagnant layer remains a part of the surface of the drug, moving wherever the drug moves. Using Fick's First Law of Diffusion, the rate of solution is the rate at which a dissolved drug diffuses through the stagnant layer for supplying drug to the drug device's reservoir's inner wall. The driving force behind the movement of the drug through the stagnant layer is the difference in concentration of the drug, $C_1$, in the stagnant layer at the surface of the drug, and the concentration $C_2$ on the farthest side of the stagnant layer. The difference in concentration $C_1 - C_2$ determines the rate at which drug is solubilized in the vehicle. Hence, if the vehicle on the farthest side contains its optimum concentration because of a low release by the drug release rate controlling wall, the rate of solubilization of new drug will be low. Correspondingly, as drug leaves the vehicle, new drug is solubilized to establish a steady state within the vehicle.

The rate of diffusion of a drug in the vehicle comprising the reservoir, is broadly determined by measuring the rate of a drug transferred from one chamber through a sintered glass filter of known pore size and thickness into another chamber and calculating from the obtained data the drug transfer rate. The method is carried out by adding to a first conical flask equipped with a ground glass stopper and a stirring bar, a measured amount of vehicle and simultaneously, the drug in the same vehicle is added to a second conical flask while keeping the level of the vehicle in the two flasks the same. Next, the flasks are stirred and samples drawn at various time intervals for analysis. The measured rate of drug transport through the sintered glass filter, and the concentration difference of the drug in the two flasks is then calculated. These procedures are known to the art in *Proc. Roy. Sci. London*, Ser. A., Vol. 148, page 1935; *J. Pharm. Sci.*, Vol. 55, pages 1224 to 1229, 1966; and references cited therein. The diffusion coefficient of a drug can also be experimentally determined by using the above apparatus or similar apparatus and procedures as described in *Diffusion in Solids, Liquids and Gases*, by W. Jost, Chapter XI, pages 436, to 488, 1960, Revised Edition, Academic Press Inc., New York.

The solubility of a drug in the drug release rate controlling copolymer material comprising the wall of a drug delivery system broadly is determined by preparing a saturated solution of a given drug and ascertaining, by analysis, the amount present in a definite area of the copolymer material. For example, the solubility of the drug in the wall is determined by first equilibrating the wall material with a saturated solution of the drug at a known temperature, for example 37° C, or with a pure liquid drug, if the drug is a liquid at 37° C. Next, drug is desorbed from the saturated wall material with a suitable solvent for the drug. The resultant solution for the drug then is analyzed by standard techniques such as ultraviolet, visible spectrophotometry, refractive index, polarography, electrical conductivity and the like, and calculating from the data the concentration, or solubility of the drug in the material.

The solubility of a drug in a vehicle can be determined by various art known techniques. One method consists in preparing a vehicle, of the given drug and ascertaining by analysis the amount of drug present in a definite quantity of the vehicle. A simple apparatus for this purpose consists of a test tube of medium size fastened upright in a water bath maintained at constant temperature. The vehicle and drug are placed in the tube and stirred by means of a motor driven rotating glass spiral. After a given period of stirring, a definite weight of the vehicle is analyzed and the stirring continued for an additional period of time. If the analysis shows no increase of dissolved substance after the second period of stirring, the results are taken as the degree of solubility of the drug in the vehicle. Numerous other methods are available for the determination of the degree of solubility of a drug in a vehicle. Typical methods used for the measurement of solubility are chemical analysis, measurement of density, refractive index, electrical conductivity, and the like. Details of various methods for determining solubilities are described in United States Public Health Service Bulletin No. 67 of the Hygienic Laboratory; *Encyclopedia of Science and Technology*, Vol. 12, pages 542 to 556, 1971, McGraw-Hill Inc.; *Encyclopaedic Dictionary of Physics*, Vol. 6, pages 545 to 557, 1962, Pergamon Press Inc.; and the like.

Also, according to Frick's Law, the rate of drug solution is directly proportional to the area of the drug, A in $cm^2$, as exposed to vehicle and inversely proportional to the length of the path through which the dissolved drug molecule must diffuse. Then, the rate of solution of the drug is given by $$R = (DA/l)(C_1 - C_2)$$

wherein R is the rate of solution, D is a proportionality constant called diffusion coefficient in $cm^2$/sec. and $C_1$, $C_2$, and $l$ are as previously defined. See *Remington's Pharamaceutical Science*, 14th Ed., pages 246 to 269, 1970, Mack Publishing Company.

In practicing the invention, one can employ any drug used to treat the eye and capable of diffusing through a copolymer at a therapeutically effective rate. Suitable drugs for use in therapy with the ocular drug delivery system of the invention include, without limitation, drugs that produce a physiologically or pharmacologically localized or systemic effect or effect in animals, including warm blooded mammals, human and primates, valuable domestic household, sport or farm animals such as horses, dogs, cats, cattle, sheep and the like; or for administering to laboratory animals such as mice, monkeys, rats, rabbits and guinea pigs. The active drugs that can be administered by the novel drug delivery system of the invention include, without limitation: antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; antivirals, including idoxuridine; and other antibacterial agents such as nitrofurazone and sodium propionate; anti-allergenics such as antazoline, methapyriline, chlorpheniramine, pyrilamine and prophenpyridamine; anti-inflammatories such as hydrocortisone, hydrocortisone acetate, dexamethasone, dexamethasone 21-phosphate, fluocinolone, medrysone, prednisolone, methylprednisolone, prednisolone 21-phosphate, prednisolone acetate, fluoromethalone, betamethasone and triaminolone; decongestants such as phenylephrine, naphazoline, and tetrahydrazoline; miotics and anticholinesterases such as pilocarpine, eserine, carbachol, di-isopropyl fluorophosphate, phospholine iodide, and demecarium bromide; mydriatics such as atropine sulfate, cyclopentolate, homatropine, scopolamine, tropicamide, eucatropine, and hydroxyamphetamine; and sympathomimetics such as epinephrine.

Drugs contained in the reservoir can be in different forms, such as uncharged molecules, components of molecular complexes or non-irritating, pharmacologically acceptable derivatives thereof. For simple derivatives of the drugs such as pharmaceutically acceptable ethers, esters, amides, and the like which have desirable retention and release characteristics but which are easily hydrolyzed by body pH, enzymes to active forms, and the like, can be employed.

The amount of drug incorporated in the system varies depending on the drug, the desired therapeutic effect, and the time span for which the system provides therapy. Since a variety of systems in a variety of sizes and shapes are intended to provide dosage regimes for therapy for a variety of maladies, there is no critical upper limit on the amount of drug incorporated in the system. The lower limit too will depend on the activity of the drug and the time span of its release from the system. Thus, it is not practical to define a range for the therapeutically effective amount of drug to be incorporated in or released by the system. However, the amount of drug present in the reservoir is generally nonlimited and it is an amount equal to or larger than the amount of drug that on its release from the system is effective for bringing about the drug's effects. Generally, an ocular system will contain from 1 microgram to 100 milligrams of drug or more, for releasing the drug to the eye at art known dosage rates. For example, an ocular drug delivery system can administer 5 to 200 micrograms per hour of pilocarpine for 24 hours to an adult human, or it can administer 10 to 100 micrograms of pilocarpine for a daily dose, and the like. The above drugs are described in *Physicians' Desk Reference,* Drug Classification Index, Ophthalmologicals, page 217, and entries cited therein, Twenty-Forth Edition, 1969, Medical Economics Inc., and in *Remington's Pharmaceutical Science,* 14th Edition, 1970, published by Mack Publishing Co. Easton, Pa.

The systems of the invention are easily fabricated. When the system is in the form of a matrix with drug distributed therethrough, particles of the drug can be mixed with the copolymer, which can be in the solid, semi-solid, or liquid form at the time, and distributed therethrough by ballmilling, callendering, stirring, shaking or the like. Where the drug is chemically compatible with the monomers used to form the ethylene-vinyl ester copolymer, the drug particles can be added at this earlier stage and the ethylene-vinyl ester matrix formed in situ. The matrix, however made and having the drug particles distributed therethrough, can then be formed to a solid shape by molding, casting, pressing, extruding, drawing or like processes. Thereafter, the matrix can be cross-linked, if desired, for example, by use of irradiation. Alternatively, the matrix can be formed to the desired shape and placed in a bath of the drug or of a solvent solution of the drug which then diffuses into the matrix to provide the system. When the system is a sealed container with walls of ethylene-vinyl ester copolymer and the drug in an interior reservoir, the container can be fabricated in many ways. Preformed hollow shapes of ethylene-vinyl ester copolymer such as tubing, can be filled with drug, alone or dispersed in a suitable vehicle, and the ends sealed with plugs or by heat to form the final system. Alternatively, the drug can be laminated between sheets of the copolymer which can be sealed together with adhesive or by heat. Other encapsulation, bonding, and coating techniques conventionally used in the art can be employed. The ability to shape the copolymers into tubes, disks, films, rings and other highly reproducible shapes of controllable composition results in ready fabrication of systems with closely controlled characteristics and overcomes a significant disadvantage of previously described ocular devices. Other standard procedures, as described in *Modern Plastics Encyclopedia,* Vol. 46, pages 62 to 70, 1969, well known to those skilled in the art can be used to fabricate the drug delivery device of the invention.

In addition to its ease of fabrication, the system of the invention offer other important advantages. One of these is that diffusion of drugs, through ethylene-vinyl ester copolymers proceeds at a lower rate than through many prior art polymers such as silicone rubber. This is important because it ensures that the rate of drug administration is controlled by diffusion through these copolymers rather than by clearance from the surface of the device. In addition, the copolymers are not known to absorb lipoidal materials at the same rate from the body, as do silicone rubber membranes and some other polymers, and therefore the characteristics of the rate controlling membrane do not vary substantially with time. This permits use of systems for therapeutic programs for a couple of days, a week or more. Another added advantage of the present invention is that the copolymers seemingly do not give rise to unwanted effects when in contact with biological media.

The reservoir of the system in one embodiment of the invention, is a matrix that contacts the inner surface of the drug release rate controlling copolymer wall and supplies drug thereto. The reservoir is comprised of a liquid, semi-solid or solid matrix containing drug, and it is a material that is permeable to the passage of drug by diffusion. The matrix can be an organic, inorganic, naturally occurring or synthetic material. Examples of matrix are gelatin, starches, carbohydrates, Irish moss, hydrophilic hydrogels of esters of acrylic acid, modified collagen and like materials. Also, other commercially available matrixes permeable to the passage of drug but at a higher rate of passage than through the wall of the device are suitable for the reservoir of the device. Representative matrixes are set forth in *Remington's Pharmaceutical Science,* pages 246 to 269, 1338 to 1390 and 1627 to 1979, 1970, published by Mack Publishing Company, Easton, Pa.

The following examples are merely illustrative of the present invention and they should not be considered as limiting the scope of the invention in any way, as these examples and other equivalents thereof will become apparent to those versed in the art in the light of the present disclosure, drawings, and the accompanying claims.

EXAMPLE 1

Pilocarpine oil (200 milligrams) is placed between two films of ethylene-vinyl methyl, acetate copolymer each having a thickness of 0.004 inch and formed from an ethylene-vinyl methyl acetate copolymer with a vinyl methyl acetate content of 40% by weight. Ellipsoidal ocular inserts having a length of 1.3 cm, a width at their widest point of 4 mm, and a thickness of 0.5 mm, are heat stamped from the assemblage, with each such insert containing 2 milligrams of pilocarpine. These ocular inserts can be inserted and retained in the cul-de-sac of the conjunctiva between the sclera of the eyeball and the lid, and when in place, will release a therapeutically effective amount of pilocarpine to control glaucoma to an adult human over a period of 24 hours.

EXAMPLE 2

Ocular dispensing systems of elliptical shape for administering a drug to the eye over a prolonged period of time and having a length of 4 to 20 millimeters, a width of 1 to 15 millimeters and a thickness of 0.1 to 4 millimeters were prepared by mixing liquid polydimethylsiloxane, chloramphenicol and stannous octoate and curing the mixture at room temperature. The resulting matrix is placed in a pre-shaped and sized ethylene-vinyl methyl acetate copolymer tube and the opened end adhesively sealed to provide a solid matrix containing drug surrounded with the drug release rate controlling membrane. The system when placed in the eye produces no discomfort or irritation and releases drug in an effective amount to produce the desired effect.

EXAMPLE 3

Milled crystals of hydrocortisone are mixed with ethylene-vinyl methylacetate copolymer having a vinyl methyl acetate content of 22% by weight and the mixture ballmilled for 20 minutes to provide a uniform distribution of drug throughout the polymeric carrier. Thereafter, the resulting mixture is shaped and size adapted as a rectangle for insertion and placement in the eye.

EXAMPLE 4

The procedures set forth in the above examples are repeated in this example with the manufacturing conditions as described, except that the final shape of the ocular insert is donut, banana, circular or bean-shaped.

In summary, it will be readily appreciated that the present invention contributes to the art unobvious ocular systems having wide and practical application by the invention's use of now described ethylene-vinyl ester copolymer. As noted supra, it has now been found that copolymers can be used for the controlled release of many drugs. In contrast, highly crystalline materials such as polyethylene or materials such as partially hydrolyzed polyvinyl acetate having a profusion of side groups, do not lend themselves to use in like environments. And, while the invention has been described and pointed out in detail and with reference to operative embodiments thereof, it will be understood that those skilled in the art will appreciate that various changes, modifications, substitutions and omissions can be made without departing from the spirit of the invention. It is intended, therefore, that the invention embrace these equivalents within the scope of the claims which follow.

We claim:

1. An ocular therapeutic system for the controlled administration of drug to the eye comprising a flexible body formed of a polymeric material containing a drug capable of diffusing through the material at a therapeutically effective rate, the body shaped, sized and adapted for comfortable insertion and retention in the cul-de-sac of the conjunctiva between the sclera of the eyeball and the lid to be held in place against the eyeball by the pressure of the lid, and wherein said material comprises an ethylene-vinyl alkyl substituted acetate copolymer having the following formula:

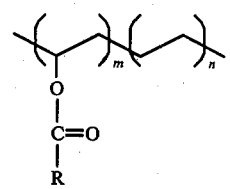

which copolymer has a vinyl alkyl acetate content $m$ of about 4 to 80% by weight, an ethylene content $n$ of $(100 - m)\%$ by weight, a melt index of about 0.1 to 1000 grams per 10 minutes, and R is an alkyl group having 2 to 7 carbon atoms.

2. The system according to claim 1 wherein the copolymer has a frequency of acyloxy groups on the polyethylene backbone of 1/200 to 1/3.5, and a density of 0.920 to 1.25.

3. The system according to claim 1 wherein the copolymer has a vinyl alkyl substituted acetate content of 4 to 50% by weight, a melt index of 0.5 to 500 grams per 10 minutes, a frequency of acyloxy groups on the polyethylene backbone of 1/150 to 1/8 and a density of 0.920 to 1.190.

4. The system according to claim 1 wherein the drug is pilocarpine.

5. The system according to claim 1 wherein the body is a container and said drug is contained in the reservoir thereof.

6. An ocular therapeutic system for the controlled administration of drug to the eye comprising a flexible body formed of a polymeric material surrounding a drug capable of diffusion through the material at a therapeutically effective rate, the body shaped, sized and adapted for comfortable insertion and retention in the cul-de-sac of the conjunctiva between the sclera of the eyeball and the eyelid to be held in place by the pressure of the eyelid, and wherein said material comprises a copolymer of the formula:

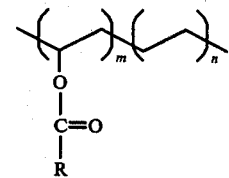

wherein R is an alkyl group of 2 to 7 carbon atoms inclusive, $m$ is (4 to 80)% by weight, $n$ is $(100 - m)\%$ by weight, and the copolymer has a melt index of about 0.1 to 1000 grams per 10 minutes.

7. The system according to claim 6 wherein the copolymer has a frequency of acyloxy groups on the polyethylene backbone of 1/200 to 1/3.5, and a density of 0.920 to 1.25.

8. The system according to claim 6 wherein the copolymer has a vinyl alkyl substituted acetate content of 4 to 50% by weight, a melt index of 0.5 to 500 grams per 10 minutes, a frequency of aceloxy groups on the polyethylene backbone of 1/150 to 1/8, and a density of 0.920 to 1.190.

9. The system according to claim 6 wherein the drug is pilocarpine.

10. An ocular therapeutic system for the controlled administration of drug to an eye of a warm blooded mammal comprising a flexible body shaped, sized and adapted for insertion and placement in the eye and formed of a non-toxic, polymeric material permeable to the passage of drug contained in the body and capable of diffusing through the material in a therapeutically effective amount, and wherein the material comprises a copolymer of the formula:

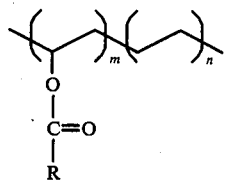

wherein R is a member selected from the group consisting of hydrogen, a lower alkyl group of 2 to 7 carbons and phenyl, $m$ is (4 to 80)% by weight and $n$ is $(100 - m)$% by weight.

11. An ocular therapeutic system for the controlled administration of drug to an eye of a warm blooded animal comprising a flexible body shaped, sized and adapted for insertion and placement in the eye and formed of a non-toxic, polymeric material permeable to the passage of drug by diffusion, the material surrounding a reservoir containing a dosage amount of drug capable of diffusion through the material in a therapeutically effective amount, and wherein said material comprises a copolymer of the formula:

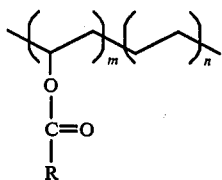

wherein R is a member selected from the group consisting of hydrogen, lower alkyl of 2 to 7 carbons and phenyl, $m$ is (4 to 80)% by weight, and $n$ is $(100 - m)$% by weight.

12. An ocular therapeutic system for the controlled and continuous administration of drug to the eye comprising a flexible body formed of a drug release rate controlling polymeric material permeable to the passage of drug by diffusion, the body adapted, shaped and sized with a length of 4 to 20 mm, a width of 0.1 to 12 mm, and a thickness of 0.1 to 4 mm for insertion and retention in the eye and containing drug therein, and wherein said material comprises a non-toxic copolymer of the formula:

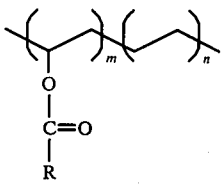

wherein R is a member selected from the group consisting of hydrogen, alkyl of 2 to 7 carbon atoms and phenyl, $m$ is (4 to 80)% by weight and $n$ is $(100 - m)$% by weight, which copolymer when in the eye administers a therapeutically effective amount of drug at a controlled rate over a prolonged period of time.

13. An ocular therapeutic system for the controlled and continuous administration of drug to the eye comprising a flexible body formed of a drug release rate controlling polymeric material permeable to the passage of drug by diffusion surrounding a reservoir containing drug, the body adapted, shaped and sized with a length of 4 to 20 mm, a width of 0.1 to 12 mm, and a thickness of 0.1 to 4 mm, for insertion and retention in the eye, the material comprising a non-toxic copolymer of the formula:

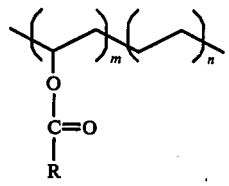

wherein R is a member selected from the group consisting of hydrogen, alkyl of 2 to 7 carbon atoms and phenyl, $m$ is (4 to 80)% by weight and $n$ is $(100 - m)$% by weight, which copolymer when in the eye administers a therapeutically effective amount of drug at a controlled rate over a prolonged period of time.

* * * * *